United States Patent [19]

Plotnikoff et al.

[11] 4,039,674

[45] Aug. 2, 1977

[54] 3-(3-METHYL-2-OCTYL)-1-[4-(1-HOMOPIPERIDINE)BUTYRYLOXY]-6,6,9-TRIMETHYL-7,8,9,10-TETRAHYDRO-6H-DIBENZO [b,d]PYRAN HYDROCHLORIDE AS AN ANTICONVULSANT AGENT

[75] Inventors: Nicholas Peter Plotnikoff, Lake Bluff; Harold Elmer Zaugg, Lake Forest, both of Ill.

[73] Assignee: Abbott Laboratories, North Chicago, Ill.

[21] Appl. No.: 677,099

[22] Filed: Apr. 15, 1976

[51] Int. Cl.² .............................................. A61K 31/35
[52] U.S. Cl. .................................................... 424/283
[58] Field of Search ......................................... 424/283

[56] References Cited

U.S. PATENT DOCUMENTS 3,941,782   3/1976   Harris et al. .......................... 424/283

Primary Examiner—Stanley J. Friedman
Attorney, Agent, or Firm—Vincent A. Mallare; Robert L. Niblack

[57] ABSTRACT

A method of preventing and/or controlling convulsions in mammalian patients comprising administering to a patient in need of such treatment a therapeutically effective amount of 3-(3-methyl-2-octyl)-1-[4-(1-homopiperidine) butyryloxy]-6,6,9-trimethyl-7,8,9,10-tetrahydro-6H-dibenzo [b,d]pyran hydrochloride.

2 Claims, No Drawings

3-(3-METHYL-2-OCTYL)-1-[4-(1-HOMOPIPERIDINE)BUTYRYLOXY]-6,6,9-TRIMETHYL-7,8,9,10-TETRAHYDRO-6H-DIBENZO [b,d]PYRAN HYDROCHLORIDE AS AN ANTICONVULSANT AGENT

DETAILED DESCRIPTION OF THE INVENTION

This invention relates to a method of preventing and/or controlling convulsions in mammalian patients using 3-(3-methyl-2-octyl)-1-[4-(1-homopiperidine)butyryloxy]- 6,6,9-trimethyl-7,8,9,10-tetrahydro-6H-dibenzo[b,d]pyran hydrochloride as an anti-convulsant agent.

The compound, 3-(3-methyl-2-octyl)-1-[4-(1-homopiperidine) butyryloxy]-6,6,9-trimethyl-7,8,9,10-tetrahydro- 6H-dibenzo[b,d]pyran hydrochloride is represented by the formula

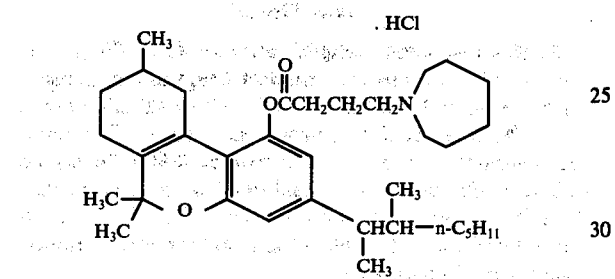

The compound can be prepared according to the method taught in U.S. application, Ser. No. 361,897 filed May 21, 1973, now U.S. Pat. No. 3,941,782.

The present compound was found to have potent anti-convulsant activity in the mouse audiogenic seizure test as well as the rat supramaximal electroshock test. In this regard, the present compound appears to exhibit the anticonvulsant profile similar to diphenylhydantoin.

One of the most outstanding properties of the present compound is the finding that marked tolerance develops to the side effects of sedation and irritability within a few days of medication. At the same time, the anticonvulsant activity of the compound is retained without any loss of the potency in the audiogenic seizure test in mice.

The oral $ED_{50}$ of the present compound for blocking the tonic extensor component of audiogenic seizures is between 1 and 2 mg./kg. daily. Complete protection against all components of audiogenic seizure in mice was seen at dosages of 1 to 5 mg./kg. The $ED_{50}$ for complete protection is approximately 2.5 mg./kg.

Thus, in the practice of this invention, 3-(3- methyl-2-octyl)-1-[4-(1-homopiperidine)butyryloxy]-6,6,9- trimethyl-7,8,9,10-tetrahydro-6H-dibenzo[b,d]pyran hydrochloride is administered to mammalian patients suffering from or prone to convulsions in oral dosages of 0.001 to 5.0 mg./kg. of body weight daily, preferably in divided doses, i.e., 3 to 4 times daily.

The present compound has been used in several tests to determine its efficacy as an anticonvulsant as compared with known anticonvulsants. In the various pharmacological tests the present compound was compared with the following compounds:

Dimethylheptylpyran (DMHP)

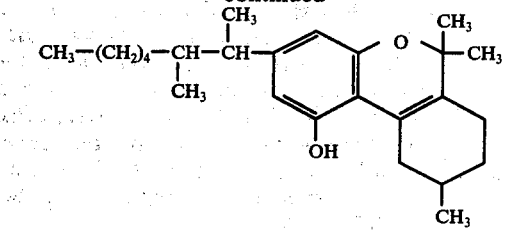

Diphenylhydantoin (DPH)

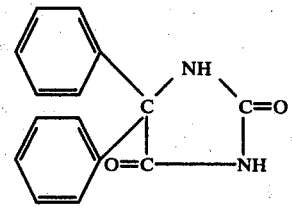

Delta-9-Tetrahydrocannabinol ($\Delta^9$-THC)

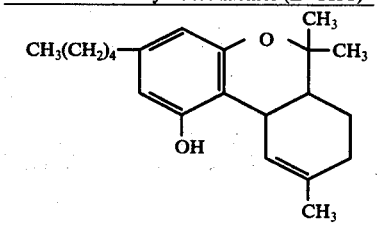

Phenobarbital

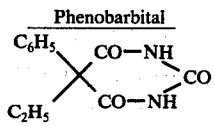

The following examples set forth the various pharmacological tests comparing the present compound's anticonvulsant activity with that of known compounds, and further illustrate the present invention and its advantages.

EXAMPLE 1

Audiogenic Seizure in Mice (Tonic Extensor Component)

In this test, male O'Grady strain mice (14–16 grams) especially bred for susceptibility to audiogenic seizures were used as subjects. The audiogenic seizure apparatus consisted of a wooden box enclosing a metal container with two doorbells attached to the upper section. The test consisted of administering the test drug orally as a suspension in 10% olive oil and 90% Methocel (0.5%) to ten animals per dose. At one, four, and twenty-four hours post drug administration the animals were placed into the audiogenic seizure test chamber and the bells activated for one minute and the animals were observed for convulsions. The test drugs included the present compound, DMHP, DPH, $\Delta^9$-THC and Phenobarbital.

As shown in Table I, below, the administration of the present compound in single oral dosages produced marked activity in antagonizing the hind limb tonic extensor component of the audiogenic seizure in mice. That is, for the present compound at one, four, and twenty-four hours post drug administration, the $ED_{50}$'s were 6.8, 1.1 and 55.9 mg./kg., respectively. Concomitantly, $\Delta^9$-THC was most active at the one hour period ($ED_{50}$ = 5.0 mg./kg.) after which the activity decreased markedly at the four and twenty-four hour periods. In contrast, DMHP was found to be active over a prolonged period (24 hours) with $ED_{50}$ values of 6.7, 2.9 and 15.1 mg./kg. at one, four and twenty-four hours respectively. In comparison, diphenyl- hydantoin (DPH) was very active at the one and four hour periods but less active at twenty-four hours, the peak effect being at the one hour post drug administration period with an $ED_{50}$ of 1.7 mg./kg. Phenobarbital, in contrast, had a peak effect at four hours post drug administration with an $ED_{50}$ of 0.3 mg./kg.

TABLE I

Comparison of Activity of Present Compound, DMPH, DPH, Δ-THC, and Phenobarbital In The Audiogenic Seizure Test at Various Time Periods

| Compound | 1 hr $ED_{50}$* mg./kg. (95% C.L.) | 4 hr $ED_{50}$* mg./kg. (95% C.L.) | 24 hr $ED_{50}$* mg./kg. (95% C.L.) | Complete Seizure Protection 4 hr $ED_{50}$* (95% C.L.) |
|---|---|---|---|---|
| Present compound | 6.8 (4.1–11.3) | 1.1 (0.5–2.4) | 55.5 (29.4–102.6) | 7.8 (4.6–13.8) |
| DMHP | 6.7 (2.1–11.0) | 2.9 (1.8–4.9) | 15.1 (8.2–26.3) | 6.7 (2.8–14.6) |
| DPH | 1.7 (1.3–2.5) | 3.3 (2.7–4.4) | 11.0 (6.5–21.6) | — |
| Δ9-THC | 5.0 (2.4–77) | 38.8 (29.1–49.3) | > 100 | 6.5** (2.9–14.6) |
| Phenobarbital | 1.9 (0.8–3.8) | 0.3 (0.1–0.9) | 6.0 (4.2–8.4) | — |

*Oral dose (mg./kg.) at which 50% of the animals are protected from hindlimb tonic extension.
**One hour data.

EXAMPLE 2

Audiogenic Seizure Test In Mice (Complete Seizure Protection)

The animals, diluent, apparatus and experimental procedure described in Example 1 above were used for the present test in mice to determine the complete seizure protection of the various compounds. The compounds tested included the present compound, DMHP and Δ9-THC.

As shown in Table I, above, the administration of the present compound in single oral doses showed activity in preventing all components of audiogenic seizures in mice, while the preconvulsive running was not antagonized. At the four hours post drug administration (peak activity), the $ED_{50}$ value was 7.8 mg./kg. Significant protection against all seizures was also found with the use of DMHP and Δ9-THC with $ED_{50}$'s respectively, of 6.7 mg./kg. and 6.5 mg./kg.

EXAMPLE 3

Audiogenic Seizure Test in Mice (5-day chronic administration)

In this test, the animals, diluent and apparatus described in Example 1, above, were used. The experimental procedure consisted of administering the test drugs orally for four days at 0.5 mg./kg. for the present compound and DMHP, and 1.0 and 0.1 mg./kg., respectively, for DPH and phenobarbital. On the fifth day of testing a dose response study (N=10 animals per dose) was initiated to obtain the $ED_{50}$ for each compound.

As shown in the results provided in Table II, below, the oral administration of the present compound to mice for five consecutive days showed marked activity in abolishing the hind limb tonic extensor component of the audiogenic seizure. At the four hours post drug administration, on the fifth day, the $ED_{50}$ of the present compound was 0.7 mg./kg. In comparison, DMHP and DPH had estimated values of $ED_{50}$'s of 1.6 and less than 0.5 mg./kg., respectively, while phenobarbital was very active with an $ED_{50}$ of 0.1 mg./kg.

TABLE II

Audiogenic Seizure Test In Mice (5 day chronic administration)

| Compound | Five Day Chronic Audiogenic Seizure Test $ED_{50}$ 4 hr* |
|---|---|
| Present Compound | 0.7 (0.01–2.1) |
| DMHP | 1.6 (0.01–4.9) |
| DPH | < 0.5 |
| Phenobarbital | 0.1 (0.01–0.2) |

*Oral dose (mg./kg.) which protects 50% of the animals from hind limb tonic extension (95% C.L.)

EXAMPLE 4

Supramaximal Electroshock Seizures In Rats (Single Oral Dose)

In this test, male Long-Evans rats (170–190 grams) were orally administered the test drugs as a suspension in olive oil and Methocel 0.5% to 5 or 10 animals per dose. At one and four hours post drug administration each animal received an electroshock (150 milliamp for 0.2 seconds) through corneal electrodes to produce a hind limb tonic extension seizure. The animals were considered protected when the hind limb tonic extensor component was blocked.

As shown in the results provided in Table III, below, the administration of the present compound in single oral doses demonstrated a marked activity in preventing the hind limb tonic extension feature of supramaximal electroshock. The $ED_{50}$ for the peak time of drug activity (four hours post administration) was 7.4 mg./kg., concomitantly the $ED_{50}$ for DMHP and Δ9-THC was 7.5 mg./kg. and 40.6 mg./kg., respectively. In contrast, DPH was much less active with an $ED_{50}$ of 62.2 mg./kg. for the same time period.

TABLE III

Supramaximal Electroshock Seizures In Rats (Single Oral Dose)

| Compound | 1 hr $ED_{50}$* mg./kg. (95% C.L.) | 4 hr $ED_{50}$* mg./kg. (95% C.L.) | 24 hr $ED_{50}$ mg./kg. (95% C.L.) |
|---|---|---|---|
| Present compound | 60.6 (38.3–98.3) | 7.4 (4.2–13.4) | > 150 |
| DMHP | 4.6 (3.0–6.9) | 7.5 (3.4–11.2) | 66.8 35 |
| Δ9-THC | 53.3 (35.5–81.4) | 40.6 (24.1–143) | > 200 |
| DPH | 23.0 (32–51.4) | 62.2 (57–67.3) | > 200 |
| Phenobarbital | 22.0 (18.7–25.0) | 18.0 (14.4–21.0) | > 40 |

*Oral dose (mg./kg.) which protects 50% of the animals from hindlimb tonic extension.

EXAMPLE 5

Supramaximal Electroshock Test In Rats (5-Day Chronic Administration)

In this test the same animals, diluent and apparatus were used as described in Example 4, above. The experimental procedure involved administering the test compounds orally at a constant dose once each day. For the present compound and DMPH, the dose was at 2.5 mg./kg., and for DPH, the dose was 30.0 mg./kg. for four consecutive days. On the fifth day a dose response study was carried out four hours after the drug administration to calculate the $ED_{50}$ for each compound tested.

As shown in Table IV, below, the chronic (5-day) oral administration of the present compound (2.5 mg./kg.), DMHP, and DPH to rats demonstrated anticonvulsant activity by abolishing the hind limb tonic extension produced by the supramaximal electroshock test. On the fifth day, 4 hours after drug administration, the $ED_{50}$'s, respectively, for the present compound and DMHP were 37.2 and 26.7 mg./kg., indicating slight tolerance. DPH was found to have an $ED_{50}$ of 26.6 mg./kg. which suggests a slower rate of tolerance. When higher doses of the present compound, such as 5.0 and 10.0 mg./kg. were administered daily, there resulted an increase in tolerance to anti-convulsant activity.

TABLE IV

Supramaximal Electroshock Test In Rats
(5-Day Chronic Administration)

| Compound | $ED_{50}$ 4 hr* mg./kg. (95% C.L.) |
|---|---|
| Present compound | 37.2 (24.0–66.0) |
| DMHP | 26.7 (5.4–118) |
| DPH | 26.6 (14.1–46.2) |

*Dose which protects 50% of the animals from hind limb tonic extension at four hours post drug administration.

The compound useful in the practice of this invention, can be formulated into various pharmaceutically acceptable doesage forms such as tablets, capsules, pills and the like for immediate or sustained release, by combining the compound with a suitable pharmaceutically acceptable carrier or diluent according to methods well known in the art. Such dosage forms may additionally include lubricants, excipients, binders, fillers, flavoring and sweetening agents and other therapeutically inert ingredients necessary for the formulation of the desired preparation.

We claim:

1. A method of preventing and/or controlling convulsions in a mammalian patient comprising administering a therapeutically effective dosage to a patient in need of such treatment orally of 3-(3-methyl-2-octyl)-[4-(1-homopiperidine)butyryloxy]-6,6,9-trimethyl-7,8,9,10-tetrahydro-6H-dibenzo[b,d]pyran hydrochloride.

2. The method of claim 1 wherein said compound is administered in dosages of from 0.001 to 5.0 mg./kg. of body weight daily.

* * * * *